(12) United States Patent
Lee et al.

(10) Patent No.: US 7,879,346 B2
(45) Date of Patent: Feb. 1, 2011

(54) COSMETIC COMPOSITIONS FOR IMPROVING THE PERFORMANCE OF TRANSFER-RESISTANT AND LONG-WEARING

(75) Inventors: Kye-Ho Lee, Seoul (KR); Jong-Hwan Kim, Gunpo (KR); Sung-Ho Chung, Seoul (KR)

(73) Assignee: STC Nara Co., Ltd., Cheonan, Chungcheongnam-do (KR)

( * ) Notice: Subject to any disclaimer, the term of this patent is extended or adjusted under 35 U.S.C. 154(b) by 49 days.

(21) Appl. No.: 11/718,447

(22) PCT Filed: Aug. 9, 2006

(86) PCT No.: PCT/KR2006/003123

§ 371 (c)(1),
(2), (4) Date: May 2, 2007

(87) PCT Pub. No.: WO2008/018644

PCT Pub. Date: Feb. 14, 2008

(65) Prior Publication Data

US 2009/0269374 A1    Oct. 29, 2009

(51) Int. Cl.
| | |
|---|---|
| A61K 8/891 | (2006.01) |
| A61K 8/895 | (2006.01) |
| A61K 8/25 | (2006.01) |
| A61K 47/02 | (2006.01) |
| A61K 47/04 | (2006.01) |
| A61K 9/14 | (2006.01) |
| A61K 8/89 | (2006.01) |
| A61Q 1/00 | (2006.01) |
| A61Q 1/02 | (2006.01) |
| A61Q 17/00 | (2006.01) |
| A61Q 17/04 | (2006.01) |

(52) U.S. Cl. .......................... 424/401; 424/59; 424/63; 424/69; 424/489; 514/769; 514/770; 514/772.3

(58) Field of Classification Search ....................... None
See application file for complete search history.

(56) References Cited

U.S. PATENT DOCUMENTS

| | | |
|---|---|---|
| 5,514,437 A | 5/1996 | Tanner et al. |
| 6,027,738 A | 2/2000 | Stepniewski et al. |
| 6,132,737 A | 10/2000 | Wolf et al. |
| 6,645,502 B2 * | 11/2003 | Sandewicz et al. ..... 424/195.15 |
| 2005/0074474 A1 * | 4/2005 | Sako .......................... 424/401 |

* cited by examiner

*Primary Examiner*—Ernst V Arnold
*Assistant Examiner*—Christopher R Lea
(74) *Attorney, Agent, or Firm*—Lexyoume IP Group, PLLC.

(57) ABSTRACT

The present invention provides a cosmetic composition including oil phase ingredients 40-90% by weight and powder ingredients 10-60% by weight. The oil phase ingredients include volatile oil 5-70 parts by weight and dimethicone/vinyl-dimethicone crosspolymer 0.1-5 parts by weight. The powder ingredients include organic hectorite 0.5-40 parts by weight, methyl methacrylate crosspolymer 0.5-5 parts by weight, and pulverulent body 0.5-50 parts by weight.

4 Claims, No Drawings

COSMETIC COMPOSITIONS FOR IMPROVING THE PERFORMANCE OF TRANSFER-RESISTANT AND LONG-WEARING

FIELD OF THE INVENTION

The present invention relates to a cosmetic composition, and, more particularly, to a cosmetic composition which has transfer-resistance, excellent long-wearing characteristics, and excellent covering and sebum controlling power, and that minimizes skin strain.

BACKGROUND OF THE INVENTION

In cosmetic compositions, a water-in-oil type emulsion is widely used as a typical formulation that includes oil phase, water phase, an emulsifier, and pigments, and that has an intermediate viscosity between a cream and a lotion. However, the water-in-oil emulsion formulation is disadvantageous for at least the following reasons: it is easily transferred after being applied on the skin, it is easily wiped away by water, particularly due to the use of a water-soluble ingredient for forming a film, and it has low long-wearing characteristics.

In the case of a solid phase cosmetic material produced from powder ingredients only, although excellent wear comfort is provided, such a solid phase cosmetic material is disadvantageous because powder is easily dispersed during application. Further, the solid phase cosmetic material is broken easily, and provides for low long-wearing characteristics.

A cosmetic material was suggested that has powder ingredients dispersed in oil phase. However, in this case, although the cosmetic material has excellent water-resistance and long-wearing characteristics, the wear comfort thereof may be described as being heavy and skin strain occurs due to the formation of a thick cosmetic film.

SUMMARY OF THE INVENTION

In order to solve the problems of the prior art described hereinabove, the present invention provides a cosmetic composition which has transfer-resistance, excellent long-wearing characteristics, and excellent covering and sebum controlling power, and that minimizes skin strain.

Also, the present invention provides a manufacturing method for the cosmetic composition that includes a mixing process which homogeneously mixes an oil phase ingredient and a powder ingredient with a mixer and a multi-step roller, adding volatile oil to the mixture, and controlling viscosity.

DETAILED DESCRIPTION OF THE INVENTION

In order to achieve the advantages described hereinabove, the present invention provides a cosmetic composition including: 40-90% by weight of an oil phase ingredient including 5-40 parts by weight of trimethylsiloxysilicate, 5-70 parts by weight of volatile oil, 0.1-5 parts by weight of dimethicone/vinyl-dimethicone crosspolymer; and 10-60% by weight of a powder ingredient including 0.5-40 parts by weight of organic hectorite, 0.5-5 parts by weight of methyl methacrylate crosspolymer, and 0.5-50 parts by weight of pulverulent body.

Also, the present invention provides a manufacturing method for the cosmetic composition including: (i) with a mixer and a multi-step roller, homogeneously mixing a) oil phase ingredients including trimethylsiloxysilicate, volatile oil, and dimethicone/vinyl-dimethicone crosspolymer, and b) powder ingredients including organic hectorite, methyl methacrylate crosspolymer, and pulverulent body; (ii) adding volatile oil to the mixture of process (i), dispersing homogeneously, and controlling viscosity.

The present invention will now be described in detail.

While researching cosmetic compositions, the inventors of the present invention found that if trimethylsiloxysilicate and dimethicone/vinyl-dimethicone crosspolymer in volatile oil were added as oil phase ingredients, the trimethylsiloxysilicate may adhere powder ingredients to the skin to thereby obtain transfer-resistance and long-wearing characteristics, and the dimethicone/vinyl-dimethicone crosspolymer may reduce skin strain. Based on these findings described hereinabove, the present invention may be accomplished.

While a water-in-oil emulsion formulation typically includes oil phase, water phase, an emulsifier, and powder (such as a pigment), a cosmetic composition of the present invention includes oil phase and powder phase, thereby obtaining a sludge formulation. The sludge formulation is such that the oil and powder phases are separated in a static state, and homogeneously mixed and remaining so for about 5 minutes when shaken prior to application. The sludge formulation is subsequently separated again after the elapse of this approximately 5-minute interval.

The cosmetic composition of the present invention does not include an emulsifier to thereby achieve reduced stickiness, wear comfort that may be described as being light when applied on the skin, and excellent water-resistance due to the fact that water phase is not included. When a cosmetic composition is mixed with a large amount of powder phase, the water-in-oil emulsion deteriorates the stability of a composition and coatibility such that uneven makeup application occurs. The cosmetic composition of the present invention, however, has the sludge formulation which may be mixed with a large amount of powder, thereby providing excellent covering and even coating.

According to the present invention, the cosmetic composition includes: a) 40-90% by weight of oil phase ingredients including 5-40 parts by weight of trimethylsiloxysilicate, 5-70 parts by weight of volatile oil, and 0.1-5 parts by weight of dimethicone/vinyl-dimethicone crosspolymer; and b) 10-60% by weight of powder ingredients including 0.5-40 parts by weight of organic hectorite, 0.5-5 parts by weight of methyl methacrylate crosspolymer, and 0.5-50 parts by weight of pulverulent body.

In the oil phase ingredients, the trimethylsiloxysilicate is an ingredient that forms a film on skin, which enables the powder ingredients to be adhered on the skin and to have transfer-resistance.

The cosmetic composition of the present invention has the oil phase trimethylsiloxysilicate added as a film-forming ingredient to thereby exhibit less transfer compared to a conventional water-in-oil emulsion formulation that uses water-soluble ingredients for the film forming. Hence, the present invention is not wiped away easily by water, and provides for excellent long-wearing characteristics.

Among the oil phase ingredients, the volatile oil is a solvent for mixing/dispersing the composition homogeneously and enhancing the coatibility of the composition. A content of the volatile oil may be determined by considering the desired dispersion and the coatibility enhancing effect of the composition.

The volatile oil may be selected from the group consisting of cyclopentasiloxane, methicone, dimethicone, C8-20 isoparaffin, propylene carbonate, polydecene, liquid paraffin, and a combination thereof.

The dimethicone has a very low viscosity, preferably within a range of 0.1-10 cps, more preferably within a range of 0.1-1.0 cps, and most preferably 0.65 cps. Also, it is preferable to use isododecane for the isoparaffin which has excellent volatility.

Further, among the oil phase ingredients, the dimethicone/vinyl-dimethicone crosspolymer is used for reducing skin strain caused by the trimethylsiloxysilicate.

A content of the dimethicone/vinyl-dimethicone crosspolymer may be determined by considering the desired reduction in skin strain.

The cosmetic composition of the present invention includes powder ingredients of 10-60% by weight to thereby possess excellent covering power compared to a conventional emulsion-type cosmetic material.

Among the powder ingredients, the organic hectorite is used for enhancing skin covering power and may be preferably selected from the group consisting of disteardimonium hectorite, quaternium-18 hectorite, stearalkonium hectorite, and a combination thereof.

Further, among the powder ingredients, the methyl methacrylate crosspolymer is excellent in sebum adsorption power, which prevents skin color from becoming dull by forming a coating layer with the sebum A content of the methyl methacrylate crosspolymer may be determined by considering the desired sebum adsorption power.

Also, among the powder ingredients, the pulverulent body adsorbs sebum, enhances skin covering ability, and is added for controlling a color of the composition, and may be preferably selected from the group consisting of iron oxide, titanium oxide, zinc oxide, talc, silica, nylon powder, and a combination thereof.

To ensure the coatibility of the composition, the pulverulent body is preferably sphere-shaped or plate-shaped. Further, preferably the pulverulent body is surface-coated with a silicon compound in order to improve the dispersion in the composition, in which the silicon compound may be selected from the group consisting of methicone, methylpolysiloxane, dimethiconol stearate, triethoxycaprylylsilane, dimethicone, and a combination thereof.

A content of the pulverulent body may be determined by considering the desired covering power, the coatibility, and the color of the cosmetic material.

The cosmetic composition of the present invention may include additives that are typically used in the art to which the present invention pertains, preferably such as a UV absorbent, a preservative, a perfume, and a combination thereof; however, the present invention is not limited in this respect.

The UV absorbent may be selected from the group consisting of ethylhexyl methoxycinnamate, octyl salicylate, benzophenone-3, benzophenone-4, benzophenone-8, gylceryl PABA, drometrizole, digalloyl trioleate, 3-(4-methylbenzylidene)camphor, menthyl anthranilate, butyl methoxydibenzoylmethane, octyl triazone, p-aminobezoic acid, and a combination thereof.

The cosmetic composition of the present invention that includes the ingredients listed hereinabove may be produced to form a liquid foundation, a cream foundation, a concealer, a sun lotion, or a sun cream.

According to the present invention, a manufacturing method of a cosmetic composition includes: (i) with a mixer and a multi-step roller, homogeneously mixing a) oil phase ingredients including trimethylsiloxysilicate, volatile oil, and dimethicone/vinyl-methicone crosspolymer, and b) powder phase ingredients including organic hectorite, methyl methacrylate crosspolymer, and pulverulent body; and, (ii) adding volatile oil to the mixture of process (i), dispersing homogeneously, and controlling viscosity.

In the process (ii), the viscosity of the composition may be variously controlled in response to an application of the cosmetic material and is not limited to any particular viscosity.

Also, in addition to the method described hereinabove, the composition may be produced by a typical manufacturing method for a cosmetic material used in the art to which the present invention pertains.

The following will describe examples of the present invention and comparative examples. However, the present invention is not limited to the examples set forth herein.

Examples 1-6

A cosmetic composition including ingredients and content ratios (% by weight) as shown in Table 1 below is produced. In more detail, ingredients 1-2 and 4-17 are weighed respectively, mixed with a high-speed mixer, and treated 3 times with a 3-step roller, thereby resulting in a mixture that is more homogeneously mixed. Subsequently, ingredient 3 is added to this resulting mixture and mixed with the high-speed mixer, thereby producing the cosmetic composition.

TABLE 1

| | Ingredient | Example | | | | | |
|---|---|---|---|---|---|---|---|
| | | 1 | 2 | 3 | 4 | 5 | 6 |
| 1 | Trimethylsiloxysilicate | 10.0 | 15.0 | 8.0 | 20.0 | 5.0 | 5.0 |
| 2 | Cyclopentasiloxane | 10.0 | 15.0 | 15.0 | 20.0 | 5.0 | 5.0 |
| 3 | Dimethicone | 26.1 | 17.1 | 36.1 | 25.2 | 47.1 | 15.1 |
| 4 | Isododecane | 19.0 | 19.0 | 9.5 | 5.0 | 9.5 | 38.0 |
| 5 | Propylene carbonate | 0.8 | 0.8 | 0.4 | 0.2 | 0.4 | 1.6 |
| 6 | Dimethicone/vinyl-dimethicone crosspolymer | 3.0 | 2.0 | 1.0 | 0.10 | 3.0 | 2.0 |
| 7 | Disteardimonium hectorite | 2.2 | 2.2 | 1.1 | 0.6 | 1.1 | 4.4 |
| 8 | Methyl methacrylate crosspolymer | 3.0 | 3.0 | 3.0 | 3.0 | 3.0 | 3.0 |
| 9 | Ethylhexyl methoxy cinnamate | 7.0 | 7.0 | 7.0 | 7.0 | 7.0 | 7.0 |
| 10 | Titanium dioxide [CI 77891] | 11 | 11 | 11 | 11 | 11 | 11 |
| 11 | Methicone | 0.1 | 0.1 | 0.1 | 0.1 | 0.1 | 0.1 |
| 12 | Iron oxides [CI 77491, CI 77492, CI 77499] | 1.2 | 1.2 | 1.2 | 1.2 | 1.2 | 1.2 |
| 13 | Talc | 4.7 | 4.7 | 4.7 | 4.7 | 4.7 | 4.7 |
| 14 | Triethoxycaprylylsilane | 0.5 | 0.5 | 0.5 | 0.5 | 0.5 | 0.5 |
| 15 | Nylon powder (Nylon-12) | 0.5 | 0.5 | 0.5 | 0.5 | 0.5 | 0.5 |
| 16 | Silica | 0.5 | 0.5 | 0.5 | 0.5 | 0.5 | 0.5 |
| 17 | Preservative | 0.4 | 0.4 | 0.4 | 0.4 | 0.4 | 0.4 |

Comparative Examples 1-6

Cosmetic compositions including ingredients and content ratios (% by weight) as shown in Table 2 below are produced. In more detail, comparative examples 1-4 are produced by the same methods of the examples 1-4. In comparative examples 5 and 6 (water-in-oil emulsion formulations), ingredients 8-17 are weighed respectively, mixed with a high-speed mixer, and treated 3 times with a 3-step roller, thereby resulting in a mixture that is more homogeneously mixed. Subsequently, a mixture that is prepared by mixing and dissolving ingredients 18-23 separately is added to this resulting mixture and mixed with the high-speed mixer, thereby producing the cosmetic composition.

TABLE 2

|   | Ingredient | Comparative Example | | | | | |
|---|---|---|---|---|---|---|---|
|   |   | 1 | 2 | 3 | 4 | 5 | 6 |
| 1 | Trimethylsiloxysilicate | — | 20.0 | 15.0 | 15.0 | — | — |
| 2 | Cyclopentasiloxane | 10.0 | 20.0 | 15.0 | 15.0 | — | — |
| 3 | Dimethicone | 36.1 | — | 38.1 | 19.1 | — | — |
| 4 | Isododecane | 19.0 | 19.0 | — | 19.0 | — | — |
| 5 | Propylene carbonate | 0.8 | 0.8 | — | 0.8 | — | — |
| 6 | Dimethicone/vinyl-dimethicone crosspolymer | 3.0 | 9.1 | 3.0 | — | — | — |
| 7 | Disteardimonium hectorite | 2.2 | 2.2 | — | 2.2 | — | — |
| 8 | Methyl methacrylate crosspolymer | 3.0 | 3.0 | 3.0 | 3.0 | 3.0 | 3.0 |
| 9 | Ethylhexyl methoxy cinnamate | 7.0 | 7.0 | 7.0 | 7.0 | 7.0 | 7.0 |
| 10 | Titanium dioxide [CI 77891] | 11 | 11 | 11 | 11 | 11 | 11 |
| 11 | Methicone | 0.1 | 0.1 | 0.1 | 0.1 | 0.1 | 0.10 |
| 12 | Iron oxides [CI 77491, CI 77492, CI 77499] | 1.2 | 1.2 | 1.2 | 1.2 | 1.2 | 1.2 |
| 13 | Talc | 4.7 | 4.7 | 4.7 | 4.7 | 4.7 | 4.7 |
| 14 | Triethoxycaprylylsilane | 0.5 | 0.5 | 0.5 | 0.5 | 0.5 | 0.5 |
| 15 | Nylon powder (Nylon-12) | 0.5 | 0.5 | 0.5 | 0.5 | 0.5 | 0.5 |
| 16 | Silica | 0.5 | 0.5 | 0.5 | 0.5 | 0.5 | 0.5 |
| 17 | Preservative | 0.4 | 0.4 | 0.4 | 0.4 | 0.4 | 0.4 |
| 18 | Cetyl PEG/PPG-10/1 Dimethicone | — | — | — | — | 3.0 | 3.0 |
| 19 | Purified Water | — | — | — | — | 62.3 | 20.1 |
| 20 | Ethanol | — | — | — | — | — | 40 |
| 21 | Glycerin | — | — | — | — | 5 | 5 |
| 22 | Polyvinyl pyrrolidone | — | — | — | — | 0.8 | — |
| 23 | Ethylcellulose | — | — | — | — | — | 3.0 |

Experimental Examples

Degrees of "transfer and water-resistance" for the examples and the comparative examples are measured by a method described hereinafter, and also "color long-wearing characteristics, transfer-resistance, and skin strain and sensation of dryness" are functionally evaluated.

Measuring the Degree of Transfer-Resistance and Water-Resistance

A) Degrees of transfer were measured by coating 0.1 g of the compositions of the examples and the comparative examples on human skin [(length)×(width)=(3 cm)×(3 cm)], and pressing the coated areas using paper sheets after the elapse of about 10 minutes. Weight changes of the paper sheets were then measured.

B) Degrees of water-resistance were measured by coating 0.1 g of the compositions of the examples and the comparative examples on artificial skin [(length)×(width)=(3 cm)×(3 cm)], and samples were deposited in water in order to intentionally wipe away the coated compositions in an automatic shaker for 1 hour. Subsequently, weight changes before and after the experiment was measured.

In order to minimize experimental errors, the processes described hereinabove were repeated 3 times respectively, and average values were taken and tabulated in Tables 3 and 4 shown below. At this time, small weight changes may be interpreted as a small degree of transfer as well as a small amount wiped away by water to thereby indicate excellent long-wearing characteristics.

TABLE 3

| Example | 1 | 2 | 3 | 4 | 5 | 6 |
|---|---|---|---|---|---|---|
| Transfer (Δmg) | 1.0 | 2.0 | 3.0 | 6.0 | 4.0 | 3.0 |
| Water-resistance (Δmg) | 0.2 | 0.7 | 1.1 | 1.2 | 3.0 | 2.1 |

TABLE 4

| Comparative Example | 1 | 2 | 3 | 4 | 5 | 6 |
|---|---|---|---|---|---|---|
| Transfer (Δmg) | 8.0 | 5.0 | 9.0 | 7.0 | 20.0 | 25.0 |
| Water-resistance (Δmg) | 2.0 | 1.3 | 1.1 | 1.1 | 15.0 | 27.0 |

As shown in Tables 3 and 4, the examples 1-6 are excellent in the degree of transfer and water-resistance compared to the comparative examples 1-6. That is, the trimethylsiloxysilicate is not added to the comparative example 1 to thereby result in increased transfer; the comparative example 2 has increased transfer due to its slow drying rate; and the comparative example 3 has a deteriorated coatibility on skin and increased transfer. Particularly, the comparative examples 5 and 6 that have the conventional water-in-oil emulsion formulations have water-soluble ingredients for the coated film, thereby exhibiting significantly deteriorated water-resistance compared to the examples 1-6.

Sensory Tests (Color Long-Wearing Characteristics, Transfer-Resistance, and Skin Strain and Sensation of Dryness)

Cosmetic compositions of the examples and the comparative examples were tested by 20 female testees aged between 20-39. About 0.5 g of the composition of the examples and the comparative examples had been used for 2 weeks, and subsequently sensory tests were made for the color long-wearing characteristics and transfer-resistance that were evaluated in three grades such as good, fair, and poor. Further, skin strain and sensation of dryness were evaluated with a number of the testees who felt skin strain and sensation of dryness.

TABLE 5

| Example | | 1 | 2 | 3 | 4 | 5 | 6 |
|---|---|---|---|---|---|---|---|
| Color long-wearing characteristics (Number of testees) | Good | 17 | 16 | 15 | 14 | 13 | 14 |
| | Fair | 2 | 3 | 2 | 3 | 5 | 5 |
| | Poor | 1 | 1 | 3 | 3 | 2 | 1 |
| Transfer-resistance (Number of testees) | Good | 18 | 17 | 16 | 13 | 12 | 11 |
| | Fair | 1 | 2 | 2 | 6 | 7 | 8 |
| | Poor | 1 | 1 | 2 | 1 | 1 | 1 |
| Skin strain and sensation of dryness (Number of testees) | | 0 | 0 | 1 | 3 | 1 | 2 |

TABLE 6

| Comparative Example | | 1 | 2 | 3 | 4 | 5 | 6 |
|---|---|---|---|---|---|---|---|
| Color long-wearing characteristics (Number of testees) | Good | 11 | 11 | 10 | 9 | 3 | 4 |
| | Fair | 8 | 7 | 9 | 10 | 12 | 10 |
| | Poor | 1 | 2 | 1 | 1 | 5 | 6 |
| Transfer-resistance (Number of testees) | Good | 10 | 11 | 9 | 8 | 2 | 3 |
| | Fair | 8 | 7 | 10 | 10 | 10 | 10 |
| | Poor | 2 | 2 | 1 | 2 | 8 | 7 |
| Skin strain and sensation of dryness (Number of testees) | | 1 | 1 | 0 | 1 | 15 | 18 |

As shown in Tables 5 and 6, the color long-wearing characteristics and the transfer-resistance of the examples 1-6 were superior to those of the comparative examples 1-6. Particularly, in the skin strain and sensation of dryness, the examples 1-6 were superior to the comparative examples 5-6 that are conventional water-in-oil emulsion formulations.

As described hereinabove, when applied to the skin, the cosmetic composition of the present invention may be adhered to the skin by the uniform film (or uniform coating layer) of non-volatile ingredients and powders that remain after volatilizing, thereby having excellent transfer-resistance, an excellent waterproof function due to possessing water-resistance, excellent long-wearing characteristics, less skin strain, and excellent covering and sebum controlling power.

What is claimed is:

1. A cosmetic composition comprising:
   oil phase ingredients comprising, with respect to the weight of the composition as a whole:
   5.0-20.0% by weight of trimethylsiloxysilicate,
   50.4-62.0% by weight of volatile oil, and
   0.1-3% by weight of dimethicone/vinyl-dimethicone crosspolymer;
   powder ingredients comprising, with respect to the weight of the composition as a whole:
   0.6-4.4% by weight of disteardimonium hectorite,
   3.0% by weight of methyl methacrylate crosspolymer, and
   18.5% by weight of pulverulent body; and
   cosmetic additives,
   wherein the volatile oil is selected from the group consisting of cyclopentasiloxane, methicone, dimethicone, C8-20 isoparaffin, propylene carbonate, polydecene, liquid paraffin, and a combination thereof,
   wherein the pulverulent body is selected from the group consisting of iron oxide, titanium oxide, zinc oxide, talc, silica, nylon powder, and a combination thereof, and
   wherein the cosmetic additives are selected from the group consisting of UV absorbent, a preservative, a perfume, and a combination thereof.

2. The cosmetic composition of claim 1, wherein the pulverulent body is surface-coated with a silicon compound selected from the group consisting of methicone, methylpolysiloxne, dimethiconol stearate, triethoxycaprylylsilane, dimethicone, and a combination thereof.

3. The cosmetic composition of claim 1, wherein the cosmetic composition is one of a liquid foundation, a cream foundation, a concealer, a sun lotion, and a sun cream.

4. A manufacturing method for the cosmetic composition of claim 1 comprising:
   (i) with a mixer and a multi-step roller, homogeneously mixing a) oil-phase ingredients comprising trimethylsiloxysilicate, volatile oil, and dimethicone/vinyl-dimethicone crosspolymer, and b) powder ingredients comprising organic hectorite, methyl methacrylate crosspolymer, and pulverulent body; and,
   (ii) adding volatile oil to the mixture of process (i), dispersing homogeneously, and controlling viscosity.

* * * * *